United States Patent [19]

Marhold et al.

[11] Patent Number: 4,620,018
[45] Date of Patent: Oct. 28, 1986

[54] BENZO-FUSED, TETRACHLORINATED HETEROCYCLIC COMPOUNDS AND A PROCESS FOR THEIR PREPARATION

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 749,151

[22] Filed: Jun. 26, 1985

Related U.S. Application Data

[62] Division of Ser. No. 638,911, Aug. 8, 1984.

[30] Foreign Application Priority Data

Aug. 11, 1983 [DE]  Fed. Rep. of Germany ....... 3329126

[51] Int. Cl.[4] .................. C07D 319/14; C07D 307/78
[52] U.S. Cl. ......................................... 549/362; 549/15; 549/49; 549/469
[58] Field of Search ............ 549/362, 434, 15, 49, 549/469, 82, 504

[56] References Cited

U.S. PATENT DOCUMENTS

| 2,816,287 | 12/1957 | Ellingboe | 549/229 |
| 2,859,245 | 11/1958 | Smith | 549/504 |
| 2,937,161 | 5/1960 | Ellingboe | 528/407 |
| 2,939,871 | 6/1960 | Pyne et al. | 549/82 |
| 4,230,864 | 10/1980 | Bailey | 549/504 |
| 4,581,466 | 4/1986 | Marhold | 549/362 |

FOREIGN PATENT DOCUMENTS

| 0607071 | 10/1960 | Canada | 549/504 |
| 0837699 | 5/1952 | Fed. Rep. of Germany | 549/504 |
| 3329126 | 2/1985 | Fed. Rep. of Germany | 549/362 |

Primary Examiner—Ethel G. Love
Attorney, Agent, or Firm—Sprung Horn Kramer & Woods

[57] ABSTRACT

Compounds of the formula

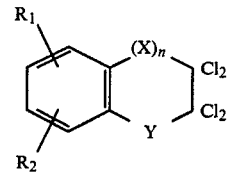

and a process for their preparation by reacting the corresponding dioxo compound with at least 2 moles of phosphorus pentachloride.

7 Claims, No Drawings

BENZO-FUSED, TETRACHLORINATED HETEROCYCLIC COMPOUNDS AND A PROCESS FOR THEIR PREPARATION

This is a division of application Ser. No. 638,911, filed Aug. 8, 1984, now pending.

The present invention relates to new chemical compounds of the formula (I)

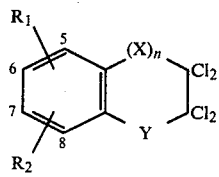
(I)

in which
R$_1$ and R$_2$ independently of one another represent hydrogen, fluorine, chlorine, bromine, COCl, CO$_2$CH$_3$, cyanide, alkyl, nitro, SO$_2$Cl, SO$_2$F, OCF$_3$, SCF$_3$, CF$_3$, CCl$_3$, CBr$_3$, phenyl, substituted phenyl, OPOCl$_2$, O-alkyl, O-aryl, S-alkyl or S-aryl or
R$_1$ and R$_2$ together represent

X and Y independently of one another represent oxygen or sulphur and
n represents zero or 1,
and a process for the preparation of these compounds.

Where R$_1$ and/or R$_2$ in the formula (I) represent substituted phenyl, they can be, for example, phenyl radicals which have 6 to 10C atoms and can be substituted by hydrogen, nitro, fluorine, chlorine, bromine, cyanide, C$_1$- to C$_4$-alkyl, SO$_2$Cl, SO$_2$F, OCF$_3$, SCF$_3$, CF$_3$, CCl$_3$ CBr$_3$, O—C$_1$- to C$_4$-alkyl or S—C$_1$ to C$_4$-alkyl.

Where R$_1$ and/or R$_2$ in the formula (I) represent alkyl, O-alkyl and/or S-alkyl, the alkyl radical can contain, for example, 1 to 4C atoms.

Where R$_1$ and/or R$_2$ in formula (1) represent O-aryl and/or S-aryl, the aryl radical can contain, for example, 6 to 10C atoms.

Preferably, in formula (I), R$_1$ and R$_2$ independently of one another represent hydrogen, fluorine, chlorine, methyl, nitro or phenyl, or R$_1$ and R$_2$ together represent

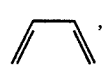

X and Y represent oxygen and n represents zero or 1.

Particularly preferably, in formula (I), R$_1$ represents hydrogen and R$_2$ represents hydrogen, nitro, methyl or phenyl, or R$_1$ and R$_2$ together represent

X and Y represent oxygen and n represents 1, or R$_1$ and R$_2$ represent hydrogen and/or nitro, Y represents oxygen or sulphur and n represents zero.

The process according to the invention for the preparation of the new chemical compounds of the formula (I)

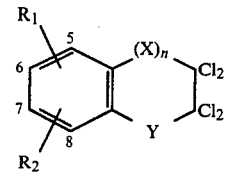
(I)

in which
R$_1$ and R$_2$ independently of one another represent hydrogen, fluorine, chlorine, bromine, COCl, CO$_2$CH$_3$, cyanide, alkyl, nitro, SO$_2$Cl, SO$_2$F, OCF$_3$, SCF$_3$, CF$_3$, CCl$_3$, CBr$_3$, phenyl, substituted phenyl, OPOCl$_2$, O-alkyl, O-aryl, S-alkyl or S-aryl or
R$_1$ and R$_2$ together represent

X and Y independently of one another represent oxygen or sulphur and
n represents zero or 1,
is characterized in that compounds of the formula (II)

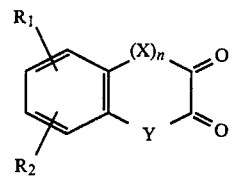
(II)

in which R$_1$, R$_2$, X, Y and n have the meaning given for formula (I), are reacted with at least 2 moles of phosphorus pentachloride at elevated temperature.

Some of the starting substances of the formula (II) are accessible according to known processes (see, for example, Chem. Ber. 45, 157 (1912), J. Indian Chem. Soc. 18, 469 (1941), Beilstein 17, 469 and Liebigs Annalen der Chemie 1975, 1545), and some are accessible in a simple manner by reaction of pyrocatechol or pyrocatechol derivatives of the formula (III)

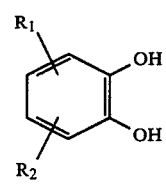
(III)

in which R$_1$ and R$_2$ have the meaning given for formula (I), with oxalyl chloride.

The reaction according to the invention of compounds of the formula (II) with phosphorus pentachloride to give the new compounds of the formula (I) can be carried out, for example, at temperatures in the range from 50° to 240° C. Temperatures in the range from 60° to 220° C. are preferred, and those in the range from 80° to 200° C. are particularly preferred.

This reaction can in general be carried out under normal pressure, but it can also be carried out under increased or reduced pressure.

The presence of solvents is not necessary in this reaction. However, in many cases it is advantageous to carry out the reaction in the presence of a solvent, for example in order to improve the stirrability of the reaction mixture and/or the removal of heat. Examples of suitable solvents are chlorinated hydrocarbons, in particular those with relatively high boiling points, such as carbon tetrachloride, chlorobenzene and dichlorobenzene. However, phosphorus oxychloride is preferably used as the solvent, since this is also formed during the reaction from the phosphorus pentachloride employed and no particular expense for its removal and recycling then results.

At least 2 moles of phosphorus pentachloride are employed per mole of a compound of the formula (II) in the process according to the invention. In general, excesses of phosphorus pentachloride do no harm. From economic considerations, the reaction is preferably carried out with 2 to 3 moles of phosphorus pentachloride per mole of a compound of the formula (II).

The chlorination according to the invention of compounds of the formula (II) has in general ended within 2 to 3 hours at reaction temperatures in the range from 80° to 200° C. At lower (higher) reaction temperaures, longer (shorter) reaction times may be advantageous. In general, longer reaction times have no adverse effect, even if excess phosphorus pentachloride is used.

In general, it is advantageous to add the phosphorus pentachloride successively in several part amounts into the process according to the invention. For example, a procedure can be followed in which about 1 mole, for example 0.8 to 1.2 moles of phosphorus pentachloride per mole of the compound of the formula (II) is first added, and, when the reaction which starts has subsided, the remainder of the phosphorus pentachloride is then added. Likewise, all the phosphorus pentachloride to be used can be taken, and the compound of the formula (II) can be added in portions.

If about 1 mole, for example 0.8 to 1.2 moles, of phosphorus pentachloride is added per mole of a compound of the formula (II), compounds of the formula (IV)

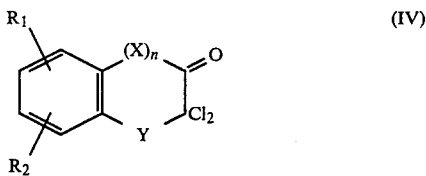

in which $R_1$, $R_2$, X, Y and n have the meaning given for formula (I), are formed.

If desired, the compounds of the formula (IV) can be isolated from the reaction mixture, for example by removing the phosphorus oxychloride formed and any solvent present and distilling or crystallizing the compounds of the formula (IV). The compounds of the formula (IV) thus isolated can then be converted into compounds of the formula (I) by further addition of phosphorus pentachloride. However, in the context of the process according to the invention, it is not necessary to isolate the compounds of the formula (IV). Preferably, in carrying out the process according to the invention, the total amount of the phosphorus pentachloride is added successively in two, preferably of approximately equal size, or several part amounts, and only the compounds of the formula (I) are isolated from the reaction mixture.

Working-up of the reaction mixture which exists after carrying out the process according to the invention is simple. The phosphorus oxychloride formed from the phosphorus pentachloride employed can be removed during and/or after the reaction by distillation, if appropriate together with the solvent present. If reaction temperatures above the boiling point of phosphorus oxychloride are to be achieved, the phosphorus oxychloride should be removed during the reaction. Last residues of phosphorus oxychloride can advantageously be removed from the reaction mixture by applying a vacuum. The residue which remains after the phosphorus oxychloride and any solvent employed have been removed can then be distilled or crystallized and the compounds of the formula (I) can thus be obtained in good yields and purities. Examples of suitable solvents for purification by crystallization are hydrocarbons, such as cyclohexane, toluene and xylene, and alcohols, such as methanol and ethanol. If appropriate, the phosphorus oxychloride removed can be used as the solvent for a further batch. Any phosphorus pentachloride added in excess and/or which has not reacted is advantageously decomposed into highly volatile compounds, for example by passing in sulphur dioxide, before the working-up operation.

The new chemical compounds of the formula (I) are useful products for preparing the insecticides described in German Offenlegungsschriften Nos. 3,023,328 and 3,023,329. For this purpose the compounds of the formula (I) are firstly fluorinated, for example in a VA steel apparatus with 1 to 800 mols of hydrogen fluoride per mol of compound of the formula (I) at 30° to 150° C. and 1 to 40 bar for 1 to 24, preferably 2 to 10 hours. The thus fluorinated compounds are then, if appropriate, nitrated, reduced and reacted with acyl isocyanates as described in German Offenlegungsschriften Nos. 3,023,328 and 3,023,329. Said insecticides can thus be prepared from starting substances which are more readily accessible and in a simpler manner than hitherto, and in good yields and purities.

It is decidedly surprising that the new compounds can be prepared in the manner according to the invention, since it is known from J.A.C.S. 77, 1137 (1955) that although keto groups can be chlorinated with phosphorus pentachloride, ester functions cannot. For example, the above reference reports that ethyl β-chloroisocrotonate, ethyl β-chlorocrotonate and unreacted ethyl acetoacetate, but no 1-methoxy-1,1,3,3-tetrachlorobutane, were obtained from the reaction of ethyl acetoacetate with phosphorus pentachloride.

The examples which follow illustrate the compounds of the formula (I) according to the invention, their preparation and their use, without in any way limiting the present invention.

EXAMPLES

Examples 1 to 11

Preparation of the starting compounds of the formula (II)

The procedure in Examples 1 to 7 was as follows:

1 mole of pyrocatechol or pyrocatechol derivatives (see Table 1) in a mixture of 500 ml of toluene and 50 ml of dioxane was taken and 1.05 mole of oxalyl chloride were added dropwise at 70° C. Thereafter, the mixture was subsequently stirred until the evolution of gas had ended. After the reaction mixture had cooled to room temperature, it was filtered and the solid product was dried in vacuo. The same results were obtained when diethyl ether or dibutyl ether was used instead of the toluene/dioxane mixture. The starting materials and the results are summarized in Table 1.

TABLE 1

| Example No. | Starting substance (benzene-1,2-diol) | Reaction product (benzodioxine-dione) | Yield (% of theory) | Melting point (°C.) |
|---|---|---|---|---|
| 1 | unsubstituted | unsubstituted | 94.5% | 186–188 |
| 2 | 3-Methyl | 5-Methyl | 78% | 136–138 |
| 3 | 5-Nitro | 7-Nitro | 67% | 180–182 |
| 4 | 5-CO₂CH₃ | 7-CO₂CH₃ | 72% | 214–217 |
| 5 | 3-Hydroxy-5-CO₂CH₃ | 5-Hydroxy-7-CO₂CH₃ | 53% | 130–132 |
| 6 | 4,5- (fused ring) | 6,7- (fused ring) | 88% | Over 250 |
| 7 | 4-Phenyl | 6-Phenyl | 84% | 160–162 |
| 7a | 3-OH | 5-OH | 71% | 138–141 |

Other starting compounds of the formula (II) were prepared in accordance with statements in the literature (see Table 2).

TABLE 2

| Example No. | Product | Literature reference |
|---|---|---|
| 8 |  | Chem. Ber. 45, 157 (1912) |
| 9 |  | J. Indian Chem. Soc. 18, 469 (1941), Beilstein 17, 467 |
| 10 |  | J. Indian Chem. Soc. 18, 469 (1941), Beilstein 17, 467 |
| 11 | 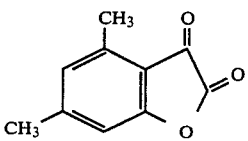 | Liebigs Annalen der Chemie 1975, 1545 |

Examples 12 to 15

Preparation of compounds of the formula (IV)

1 mole of a dicarbonyl compound was mixed with 1.05 moles of phosphorus pentachloride and the reaction mixture was warmed slowly until it became liquid. The temperature was then slowly increased and the phosphorus oxychloride formed was distilled off. In order to bring the reaction to completion, the phosphorus oxychloride was removed slowly by means of a reflux separator and the internal temperature of the reaction mixture was brought up to 200° C. Residual phophorus oxychloride was removed by applying a vacuum. The reaction products were purified by distillation (in which case the boiling point is given) or by crystallization from cyclohexane/toluene (in which case the melting point is given). The starting materials and the results are summarized in Table 3.

TABLE 3

| Example No. | Starting substance | Reaction product | Yield (% of theory) | Boiling or melting point (°C.) |
|---|---|---|---|---|
| 12 | unsubstituted | unsubstituted | 96% | 130–132/16 mbar (boiling point) |
| 13 | 6,7- (fused ring) | 6,7- (fused ring) | 87% | 170–172 (melting point) |
| 14 | 7-Methyl | 7-Methyl | 67% | 142–145/18 mbar (boiling point) |
| 15 | 6-Phenyl | 6-Phenyl | 89% | 180–184/0.6 mbar (boiling point) |

Examples 16 to 21

Preparation of compounds of the formula (I)

1 mole of the particular starting compound of the formula (II) given was mixed with 1 mole of phosphorus pentachloride and the mixture was heated until it had become liquid. A further 1.2 moles of phosphorus pentachloride were then added and distillated removal of the phosphorus oxychloride formed was started. During this, the temperature was gradually increased up to 190° to 200° C., in order to distil over residues of phosphorus oxychloride. The residue was either distilled (in which case the boiling point is given) or crystallized from methanol (in which case the melting point is given). The starting substances and the results are summarized in Table 4.

TABLE 4

| Example No. | Starting substance | Reaction product | Yield (% of theory) | Boiling or melting point (°C.) |
|---|---|---|---|---|
| 16 | unsubstituted | unsubstituted | 92% | 140–142/20 mbar (boiling point) |
| 17 | 7-Nitro | 7-Nitro | 81% | 81–82 (melting point) |
| 18 | 8-Methyl | 8-Methyl | 72% | 158–162/20 mbar (boiling point) |
| 19 | 6-Phenyl | 6-Phenyl | 84% | 115–117 (melting point) |
| 20 | 6,7- (fused alkene) | 6,7- (fused alkene) | 88% | 175–178 (melting point) |
| 21 | (benzofuran-dione) | (chlorinated benzofuran) | 47% | 54–56 (melting point) |

Example 22

Use of compounds of the formula (I)

150 ml of hydrogen fluoride were initially introduced into a VA steel fluorinating apparatus, and 50 g of 6-nitro-2,2,3,3-tetrachloro-1,4-benzodioxene were added at 0° C. 3 bar of nitrogen were then forced in, the mixture was heated at 60° C. for 3 hours and at 100° C. for a further 2 hours and then cooled and let down, 1 ml of antimony pentachloride was added, 3 bar of nitrogen were again forced in and the mixture was heated at 120° C. for a further 3 hours. After cooling, the batch was discharged onto ice, the organic phase was taken up in methylene chloride and the mixture was washed with water, dried and distilled. 26 g of nitro-2,2,3-trifluoro-3chloro-1,4-benzodioxene of boiling point 125° to 130° C. under 20 mbar were obtained. This compound was converted, as described in German Offenlegungsschrift No. 3,023,328, to the acylureas of outstanding insecticidal action described therein.

What is claimed is:

1. Process for the preparation of compounds of the formula in which $R_1$ and $R_2$ independently of one another represent hydrogen, fluorine, chlorine, bromine, COCl, $CO_2CH_3$, cyanide, alkyl, nitro, $SO_2Cl$, $SO_2F$, $OCF_3$, $SCF_3$, $CF_3$, $CCl_3$, $CBr_3$, phenyl, substituted phenyl, $OPOCl_2$, O-alkyl, O-aryl, S-alkyl or S-aryl or, $R_1$ and $R_2$ together represent

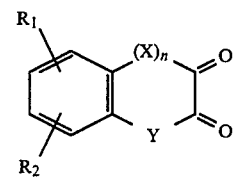

X and Y independently of one another represent oxygen or sulphur and n represents zero or 1, wherein compounds of the formula in which $R_1$, $R_2$, X, Y and n have the above-mentioned meaning, are reacted with at least 2 moles of phosphorus pentachloride at elevated temperature.

2. Process according to claim 1, wherein the reaction is carried out at temperatures in the range from 50° to 240° C.

3. Process according to claim 2, wherein the reaction is carried out at temperatures in the range from 80° to 200° C.

4. Process according to claim 1 wherein 2 to 3 moles of phosphorus pentachloride are employed per mole of the compound of the formula

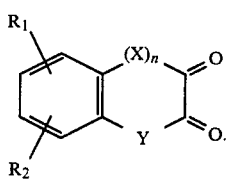

5. Process according to claim 1 wherein the phosphorus pentachloride is added successively in several part amounts.

6. Process according to claim 1 wherein 0.8 to 1.2 moles of phosphorus pentachloride are first added per mole of compound of the formula

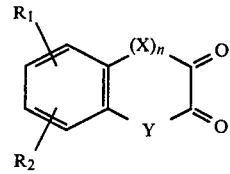

and compounds of the formula

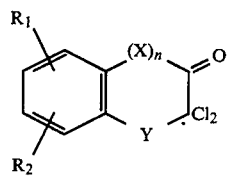

in which $R_1$, $R_2$, X, Y and n have the meaning given in claim 1, are thus prepared, and the compounds of the formula

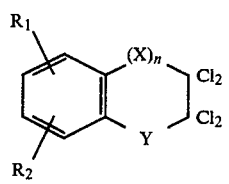

are prepared therefrom by further addition of phosphorus pentachloride.

7. Process according to claim 1 wherein the reaction is carried out in the presence of phosphorus oxychloride as the solvent.

* * * * *